United States Patent
Nordrum et al.

(10) Patent No.: US 11,135,251 B2
(45) Date of Patent: *Oct. 5, 2021

(54) METHODS FOR IMPROVING FILLET QUALITY IN FARMED FISH

(71) Applicant: Aker BioMarine Antarctic AS, Stamsund (NO)

(72) Inventors: Sigve Nordrum, Slependen (NO); Lars Thomas Poppe, Trondheim (NO); Thomas Larsson, Ås (NO); Turid Mørkøre, Ås (NO)

(73) Assignee: Aker BioMarine Antarctic AS, Stamsund (NO)

( * ) Notice: Subject to any disclaimer, the term of this patent is extended or adjusted under 35 U.S.C. 154(b) by 287 days.

This patent is subject to a terminal disclaimer.

(21) Appl. No.: 14/728,101

(22) Filed: Jun. 2, 2015

(65) Prior Publication Data

US 2015/0343000 A1 Dec. 3, 2015

Related U.S. Application Data

(60) Provisional application No. 62/006,438, filed on Jun. 2, 2014.

(51) Int. Cl.
| | |
|---|---|
| *A61K 35/612* | (2015.01) |
| *A01K 61/10* | (2017.01) |
| *A23K 40/25* | (2016.01) |
| *A23K 40/20* | (2016.01) |
| *A23K 20/111* | (2016.01) |
| *A23K 10/22* | (2016.01) |
| *A23K 50/80* | (2016.01) |
| *A23L 17/00* | (2016.01) |

(52) U.S. Cl.
CPC ............ *A61K 35/612* (2013.01); *A01K 61/10* (2017.01); *A23K 10/22* (2016.05); *A23K 20/111* (2016.05); *A23K 40/20* (2016.05); *A23K 40/25* (2016.05); *A23K 50/80* (2016.05); *A23L 17/00* (2016.08)

(58) Field of Classification Search
None
See application file for complete search history.

(56) References Cited

U.S. PATENT DOCUMENTS

2012/0040076 A1* 2/2012 Nichols .................. A23K 10/22
426/601

FOREIGN PATENT DOCUMENTS

CA 2169887 9/1996

OTHER PUBLICATIONS

Ringo et al. (2006) Aquaculture Research, 37, 1644-1653.*
Olsen et al. (2006) Aquaculture Nutrition, 12, 280-290.*
Kubitza et al. (1997) Aquaculture 148: 299-312.*
Spark et al. (1982) JAOCS, vol. 59, No. 4. 185-188.*
Suontama et al. (2007) Aquaculture Nutrition, 13; 50-58.*
Yoshitomi et al. (2006) Aquaculture 261: 440-446.*
Sorensen (2012) Aquaculture Nutrition, 18, 233-248. (Year: 2012).*
Carter, C.G., Hauler, R.C. and Foster, C. (Eds.) 2002 Aquaculture Feed Development for Atlantic Salmon (*Salmo salar*). Fisheries Research and Development Corporation Project No. 1998/322. Fisheries Research and Development Corporation: Deakin, Austrailia. (Year: 2002).*
Website document entitled: Atlantic salmon—Feed Production (available at www.fao.org/fishery/affris/species-profiles/atlantic-salmon/feed-production/en/) Downloaded Sep. 12, 2019. (Year: 2014).*
Foroutani et al. (2018) PLoS ONE 13(9):e0198538. 14 pages (Year: 2018).*
Ytrestoyl et al. (2015) Aquaculture 448: 365-374. (Year: 2015).*
Andersen et al. "Fillet gaping in farmed Atlantic salmon (*Salmo salar*)." 1994, Norwegian Journal of Agricultural Sciences 8, 165-179.
Folkestad et al. "Rapid and non-invasive measurements of fat and pigment concentrations in live and slaughtered Atlantic salmon (*Salmo salar* L.)." Aquaculture, 2008, 280, 129-135.
International Search Report and Written Opinion, International Patent Application No. PCT/IB2015/001258, dated Jan. 26, 2016.
Johnston et al. "Fast growth was not associated with an increased incidence of soft flesh and gaping in two strains of Atlantic salmon (*Salmo salar*) grown under different environmental conditions" Aquaculture, vol. 265, No. 1-4, 2007, pp. 148-155.
Midtlyng et al. "Experimental studies on the efficacy and side-effects of intraperitoneal vaccination of Atlantic salmon (*Salmo salar* L.) against furunculosis." 1996, Fish & Shellfish Immunology 6, 335-350.
Moren M. et al. "Element concentrations in meals from krill and amphipods,—Possible alternative protein sources in aomplete diets for framed fish", Aquaculture, vol. 261, No. 1, 2006, pp. 174-181.
Mørkøre et al. "Relating sensory and instrumental texture analyses of Atlantic salmon." Journal of Food Science, 2003, 68, 1492-1497.
Patrick, K. "Wild Pacific Salmon Explained—NatrualNews.com", Apr. 1, 2009, retrieved from the internet: URL: http://www.naturalnews.com/025969_salmon_fat_fish.html.
Storebakken, Trond "Krill as a potential feed source for salmonids" Aquaculture, vol. 70, No. 3, 1988, pp. 193-205.
Yoshitomi B. et al. "Evaluation of krill (Euphausia superba) meal as a partial replacement for fish meal in rainbow trout Oncorhynchuse mykiss) diets" Aquaculture, vol. 261, No. 1, 2006, pp. 440-446.

* cited by examiner

*Primary Examiner* — Russell G Fiebig
(74) *Attorney, Agent, or Firm* — Casimir Jones, S.C.; J. Mitchell Jones

(57) ABSTRACT

The present invention provides methods for improving flesh quality in farmed fish, and in particular decreasing gaping in fillets from farmed fish as well as increasing flesh and fillet firmness.

5 Claims, 1 Drawing Sheet

METHODS FOR IMPROVING FILLET QUALITY IN FARMED FISH

FIELD OF THE INVENTION

The present invention provides methods for improving flesh quality in farmed fish, and in particular decreasing gaping in fillets from farmed fish as well as increasing flesh and fillet firmness.

BACKGROUND OF THE INVENTION

Fish consumption is on the increase around the world. According to the National Marine Fisheries Services, the amount of commercially caught fish (fin- and shell-fish), measured as "edible meat" consumed per person in the United States, increased from 11.2 lbs (~5.08 kg) in 1910 to 16.6 lbs (~7.53 kg) in 2004. Salmon consumption in the United States increased nine-fold between 1987 and 1999; during that time total European salmon consumption increased more than four times. Between 1992 and 2002, salmon consumption in Japan doubled. There are many reasons for this increase, including competitive pricing, the perception that eating fatty fish is healthy, and a general increase in fish consumption. Atlantic salmon is a good source of protein, with almost 20 grams per 100 gram serving, and is an excellent source of omega-3-fatty acids, which are thought to aid in cardiovascular health.

It is desirable for farmed salmon to utilize nutrients in food to muscle building rather than the deposition of fat in the abdominal cavity. Low intestine percentage provides high harvest yield and good muscle fullness increase fillet yield. Organ adhesions have been largely linked to the vaccine/immunization, but recently it has been observed that the feed composition can be a significant contributing factor. Severe adhesion of organs has been shown to cause growth inhibition. Visible fat deposition around the heart and fatty liver are other factors that have received increased attention in recent times. Fat accumulation in and around organs can cause metabolic problems and an efficient metabolism has been shown to be important for fillet quality. Significant quality characteristics for fillets include fat content and fatty acid composition, fillet color, firmness, and absence of gaps between muscle segments (gaping). Furthermore, smell and taste as well as good storage stability are important quality characteristics.

SUMMARY OF THE INVENTION

The present invention provides methods for improving flesh quality in farmed fish, and in particular decreasing gaping in fillets from farmed fish as well as increasing flesh and fillet firmness.

In some embodiments, the present invention provides methods of improving a parameter of flesh quality in fish comprising: feeding fish a dietary ration comprising an amount of krill meal effective to improve one or more parameters of flesh quality in said fish. In some embodiments, the improvement in a parameter flesh quality is selected from the group consisting of one or more of decreased fillet gaping, increased flesh and fillet firmness, decreased soft muscle, decreased muscle pH, increased harvest yield and increased fillet yield. In some embodiments, the improvement in a parameter of flesh quality is decreased fillet gaping. In some embodiments, the improvement in a parameter of flesh quality is increased flesh and fillet firmness. In some embodiments, the improvement in a parameter of flesh quality is decreased soft muscle. In some embodiments, the improvement in a parameter of flesh quality is decreased muscle pH. In some embodiments, the improvement in a parameter of flesh quality is increased harvest yield or increased fillet yield.

In some embodiments, the ration is a pelleted ration. In some embodiments, the krill meal comprises an antioxidant. In some embodiments, the antioxidant is a synthetic antioxidant. In some embodiments, the synthetic antioxidant is ethoxyquin. In some embodiments, the ration comprises from about 4% to 15% krill meal.

In some embodiments, the present invention provides methods of improving a parameter of flesh quality in fish comprising: feeding fish a pelleted dietary ration comprising an amount of krill meal effective to improve one or more parameters of flesh quality in said fish, wherein said improvement in a parameter flesh quality is selected from the group consisting of one or more of decreased fillet gaping, increased flesh and fillet firmness, decreased soft muscle, decreased muscle pH, increased harvest yield and increased fillet yield. In some embodiments, the fish are fed the preferred rations during the grow out period, i.e., when the fish are from about 14 to 24 months of age.

In some embodiments, the present invention provides methods of decreased fillet gaping in a population of fish comprising feeding said population of fish a dietary ration comprising an amount of krill meal effective to decrease fillet gaping under conditions such that fewer than 10% of fish from said population have gaping score of greater than 2.0 points (visible cleavage).

In some embodiments, the methods described above further comprise the step of evaluating, or causing to have evaluated, one or more parameter of flesh quality following feeding and processing (e.g., slaughtering) of a portion of a population of farmed fish fed the ration comprising krill meal. In some embodiments, the flesh quality is evaluated by determining one or more of the gaping score, fillet firmness, fillet pH, amount of soft muscle, fillet yield, and harvest yield, preferably as described herein. In some embodiments, the parameter is evaluated for the Norwegian Quality Cut (NQC).

DETAILED DESCRIPTION OF THE INVENTION

Figure 1A:
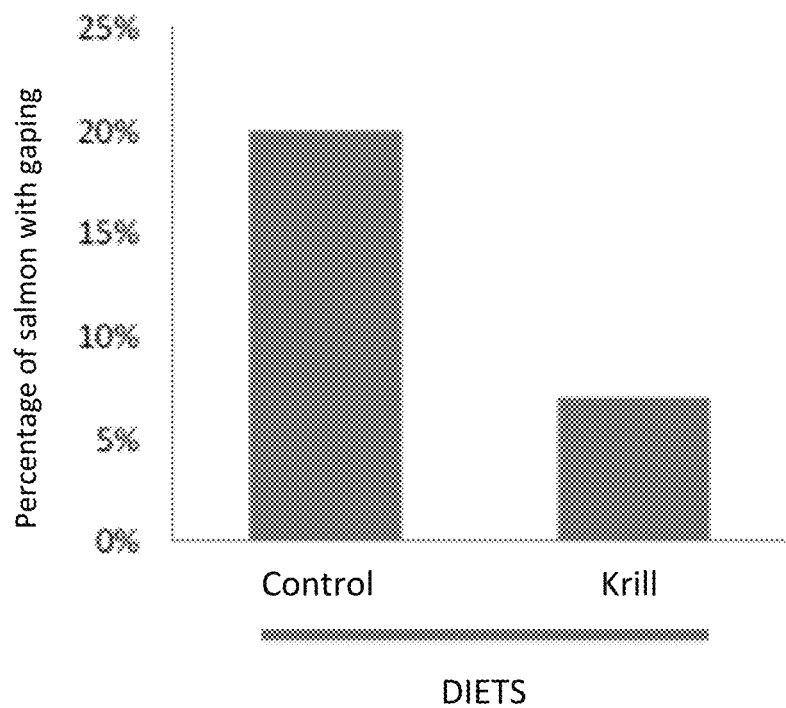
FIGS. 1A and 1B. Percentage of salmon with visible gaping (a) and soft texture (b)
Figure 1B:
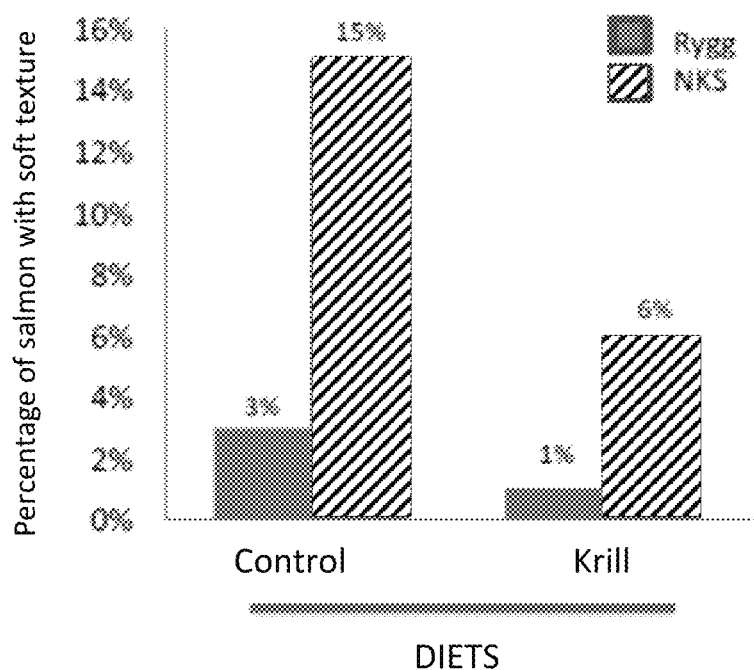

The present invention provides methods for improving flesh quality in farmed fish, and in particular decreasing gaping in fillets from farmed fish as well as increasing flesh and fillet firmness. Accordingly, in some embodiments, the present invention provides methods of improving a parameter of flesh quality in fish (e.g., a population of fish) comprising: feeding fish a dietary ration comprising an amount of krill meal effective to improve one or more parameters of flesh quality in said fish.

The salmon farming production cycle is about 3 years. During the first year of production the eggs are fertilized and the fish is grown into approximately 100 grams in controlled freshwater environment. Subsequently, the fish is transported into seawater cages where it is grown out to approximately 4-5 kg during a period of 14-24 months. The growth of the fish is heavily dependent on the seawater temperatures, which varies by time of year and across regions.

Having reached harvestable size, the fish is transported to primary processing plants where it is slaughtered and gutted. The present invention provides rations that are especially useful during the grow out period, i.e., when the fish are from about 14 to 24 months of age.

In some embodiments, the improvement in flesh quality is a decrease in gaping in fillets obtained from the fish. In preferred embodiments, gaping is evaluated on a scale from zero to five, where zero indicates no cleavage and five maximum cleavage (Andersen et al. 1994). A gaping score of 2.0 indicates visible cleavage. In some embodiments, less than 10% of the fish in a population being fed a ration containing an effective amount of krill meal produce fillets which have a gaping score of 2.0 or higher.

In some embodiments, the improvement in a parameter of flesh quality is increased flesh and fillet firmness, preferably as measured by strength of the fillet. In some embodiments, the strength in fillets is measured instrumentally (Texture Analyzer TA-XT2) as the force (Newton, N) that was needed to break through fillet surface (fracture strength) of a cylinder (12.5 mm in diameter). The preferred unit for strength is N*s. In some embodiments, the fish in a population being fed a ration containing an effective amount of krill meal have produce fillets with an average fillet strength of from 240 to 280 N*s.

In some embodiments, the improvement in a parameter of flesh quality is decreased soft muscle. In some embodiments, the less than 14%, 12% or 10% of fish in a population being fed a ration containing an effective amount of krill meal produce fillets with soft muscle. In some embodiments, fillets with soft muscle are those exhibiting a strength of less than or equal to 6.0 N.

In some embodiments, the improvement in a parameter of flesh quality is decreased muscle pH. In some embodiments, fish in a population being fed a ration containing an effective amount of krill meal produce fillets with an average muscle pH of from 6.03 to 6.06.

In some embodiments, the improvement in a parameter of flesh quality is increased harvest yield or increased fillet yield.

Typical salmon rations of the invention comprise from about 5% to 50% fish meal, 4% to 15% krill meal, 5% to 30% vegetable oil and 5%45% fish oil, expressed as % weight of component/weight of the ration (% w/w). In some embodiments, the rations have a crude protein content of from about 32% to 46%, preferably from about 36% to 42%, a crude lipid content of from about 26% to 42%, preferably from about 28% to 38%, a carbohydrate (NFE) content of from about 11% to 18%, preferably from about 13% to 15%, a fiber content of from about 1% to 5%, preferably from about 1.5% to 2.5%, an ash content of from about 4% to 7%, preferably about 4.5% to 6.5%, a total phosphorus content (P) of from about 0.5% to 1.1%, preferably about 0.6% to 1.0%, a gross energy content of from about 20 to 30 MJ/kg, preferably from about 23 to 28 MJ/kg, and a digestible energy content of from about 20 to 24 MJ/kg. Typical components of a salmon ration will contain krill meal in amount of about 4 to 15%, with the remaining requirements being met by, for example, fish meal, fish oil, vegetable oil (e.g., rapeseed or soybean oil), wheat gluten, wheat, soya cake, sunflower cake, and horse beans. The rations may further be supplemented with vitamins and minerals.

In some preferred embodiments, the ration is a pelleted ration. The pellet sizes may preferably range from about 4 mm to 12 mm, and most preferably from about 6 mm to 10 mm.

In some preferred embodiments, the rations comprise krill meal, most preferably from about 1% to 65% w/w krill meal, preferably 2% to 40% w/w krill meal, more preferably from about 3% to 30% w/w krill meal, and most preferably about 4% to 15% w/w krill meal, expressed as % weight of krill meal/weight of the ration (% w/w). In some preferred embodiments, the krill meal is prepared from whole grinded and dried *Euphausia superba*. In some embodiments, the krill meal comprises an antioxidant. In some embodiments, the antioxidant is a synthetic antioxidant. In some embodiments, the synthetic antioxidant is ethoxyquin, and is included in amount of from about 100 to 300 mg/kg, preferably from about 150 to 250 mg/kg. In preferred embodiments, the krill meal comprises from about 48% to 68% w/w, preferably 53% to 63% w/w crude protein, from about 15% to 35% w/w, preferably 18% to 28% w/w total fat, from about 4% to 8% w/w water, and from about 8% to 14% w/w ash, expressed as % weight of component/weight of the meal (% w/w). In some embodiments, the fat comprises from about 30% to 50% w/w, preferably about 35% to 45% w/w phospholipids, expressed as % weight of phospholipids/weight of the total fat (% w/w). In some embodiments, the fat comprises from about 15% to 31% w/w, preferably from about 19% to 27% w/w omega-3 fatty acids, expressed as % weight of omega-3 fatty acids/weight of the total fatty acids (% w/w). In some embodiments, the ratio of EPA to DHA fatty acids in the fat is from about 3:1 to 1.5:1, and preferably from about 2.5:1 to 1.8:1.

EXPERIMENTAL

Farmed salmon that were fed a standard ration or the same feed supplemented with krill meal were used in this study. The salmon were reared at five different locations and a total of 260 salmon were analyzed for the period. The following characteristics were evaluated: body shape (condition factor), carcass yield, fillet yield, macroscopic condition of organs and organ adhesions, heart and liver index and visible amount of visceral fat. The fillets were examined for the following quality properties: fat content, pH, color, firmness and gaping. Fish material was sent to Nofima for analysis.

The fish fed standard feed without krill meal (control group) weighed 4.3 kg while the fish given feed mixed krill meal (krill group) weighed 4.6 kg (P<0.05). The condition factor was 1.3 for both groups.

Organ assessments showed no significant differences between the groups, with the exception of liver color that was significantly paler for the Krill group. Both groups had relatively little visceral fat compared to what is usually seen in harvested fish (2.3 points for both groups). Intestinal mass was lower for Krill group, which was consistent with the 1.4% percentage points higher harvest yield (90.1% for Krill group vs. 88.7% for control group). Fillet yield for the krill group was 2.7 percentage points higher than for the control group. The higher fillet yield for krill group (63.7% vs. 60.8%) coincided with significantly better filet fullness (4-5% thicker fillets measured instrumentally).

Fillet quality was generally good. Average fillet color (SalmoFan points and fat content were respectively 27.2 points and 19.1%. Instrumental texture measurements showed that the krill group had higher average strength and the percentage of fillets with soft texture and gaping was lower.

The results of this study show that fish fed with feed supplemented with krill meal are stimulated to produce more and firmer muscle resulting in higher harvest yield and fillet yield and reduced proportion fillets with soft muscle and gaping. Incorporation of krill meal in salmon feed showed no negative effects on the overall fish material that was analyzed.

Materials and Methods.

Over a several month period, salmon from several different locations receiving the control and test diets were sent to Nofima for examination.

Whole fish were opened and scored for adhesions (Speilberg scale, Midtlyng et al, 1996). Abdominal fat was measured using a well-established scale (1-5) where 1=pyloric caeca well visible through the fat, and 5=pyloric caeca totally covered and with no visible structure from caecae. Pigmentation in organs was assessed visually using standard scale (0-3, where 0=no melanin, 3=completely black). Gender was recorded. Liver color was recorded as well as the general impression of the organs. Round weight, gutted weight, fillet weight and body length were recorded. Slaughter yield, fillet yield, cardiac index and liver index was also calculated (100*gutted weight, weight of fillet, heart or liver (g)*live weight (g)−1).

Gaping was evaluated on a scale from zero to five, where zero indicates no cleavage and five maximum cleavage (Andersen et al. 1994) (FIG. 3). Color (SalmoFan), pigment (mg/kg) and fat (%) in fillets were analyzed by image analysis (Folkestad et al., 2008). Strength in fillet was measured instrumentally (Texture Analyzer TA-XT2) as the force (Newton, N) that was needed to break through fillet surface (fracture strength) of a cylinder (12.5 mm in diameter). This parameter has previously shown good correlation with sensory perceived strength (Mørkøre and Einen 2003). Fillet Height (mm) was also measured. Analyses were made in the back muscle (loin) and the Norwegian quality cut (NQC) over the sideline. pH was measured at these positions as well.

Fully mature fish were excluded from the fish material analyzed. Gender had a significant effect on several parameters, and was therefore included in the statistical models where it was relevant. Non-parametric tests were used for nonparametric variables e.g., Speilberg score, gaping, etc.). In case gender had an effect on these variables, the Bonferroni Multiple Comparisons was used to test the effect of feed type. All other variables were tested for the effect of feed type by ANOVA. The significance level was set at 5%.

Results.

Biometric Characteristics.

The average weight of the total fish material was 4.5 kg (range from 2.1 kg to 7.6 kg). Salmon from the krill group were 310 g heavier than salmon from the control group, and this difference was significant (4.65 kg vs. 4.34 kg). Salmon from the krill group also had significantly higher gutted weight (4.48 kg vs. 4.04 kg), but the difference in body length was not significant. The salmon that received feed mixed krill meal had significantly higher harvest yield (1.4% units), but the condition factor showed no significant difference between fish groups (1.25 to 1.26) (see Table 1). Fish length was measured either by slaughterhouses or on arrival at the laboratory. There may be a contributing factor to some uncertainty for calculations of body shape (condition factor).

TABLE 1

| Attribute | Control group | Krill group | P value |
| --- | --- | --- | --- |
| Round weight (kg) | 4.34 ± 0.12 | 4.65 ± 0.10 | 0.0449 |
| Gutted weight (kg) | 4.04 ± 0.12 | 4.48 ± 0.09 | 0.0024 |
| Body length (cm) | 72.0 ± 0.7 | 72.9 ± 0.6 | 0.3369 |
| Condition factor | 1.24 ± 0.01 | 1.26 ± 0.01 | 0.3526 |
| Yield | 88.7 ± 0.3 | 90.1 ± 0.2 | 0.0006 |

Organs and Visceral Fat.

All fish had low levels of adhesions of the organ package (score 1 on average (scale goes to score 6)) and no abnormal deposition of melanin was observed (a score of 1 is considered normal for farmed salmon). Salmon from both groups had relatively low deposition of fat in the abdominal cavity, with an average score of 2.3. This means that the pyloric caeca were visible through the visceral fat depots. There was no indication of differences between groups (Table 2). Weight records of the intestines showed that these were significantly heavier for the control group. The size of the liver and heart were normal and there was no significant difference between groups. The salmon in the krill group had significantly lower scores for liver color, meaning the color was pale. The difference in the liver color was equivalent to 0.2 points, which is a small difference and difficult for the eye to detect.

TABLE 2

| Attribute | Control group | Krill group | P value |
| --- | --- | --- | --- |
| Speilberg score | 1.0 ± 0.1 | 0.8 ± 0.1 | 0.2718 |
| Melanin in organs (points) | 0.9 ± 0.06 | 0.9 ± 0.05 | 0.2835 |
| Fat around organs (points) | 2.3 ± 0.1 | 2.3 ± 0.1 | 0.8988 |
| Liver color (points) | 1.9 ± 0.1 | 1.7 ± 0.1 | 0.0014 |
| Liver index (%) | 0.96 ± 0.02 | 0.96 ± 0.02 | 0.9714 |
| Cardiac index (%) | 0.12 ± 0.00 | 0.13 ± 0.00 | 0.6491 |

Fillet Quality.

Fillet yield was significantly higher in the krill group (63.7%) compared with the control group (60.8%) (Table 3). This is a significant difference and coincided with significantly thicker fillets of fish fed with the krill meal supplemented feed. Fillet color ranged from 25 to 29.5 on the SalmoFan scale, and was 27.4 on average for both groups combined. An average color score of 27 is considered very good. There were no significant differences between groups with regard to fillet color or pigment levels in muscle. Fat content in muscle was 1.19 on average, and was similar between groups.

The control group had a significantly higher degree of gaping than the krill group. The percentage of the salmon with gaping over two points (visible cleavage) was 20% and 7%, respectively, in the control group and Krill group. The krill group had significantly lower pH, suggesting a higher energy state (greater glycogen stores in the live fish). Low pH often coincides with more gaping, but not for this fish material. It shows that gaping has a complex causation, and it is conceivable that the salmon from krill group had stronger and/or more connective tissue in muscle.

TABLE 3

| Attribute | Control group | Krill group | P value |
| --- | --- | --- | --- |
| Fillet yield (%) | 60.8 ± 0.6 | 63.7 ± 0.5 | 0.0003 |
| Gaping | 1.7 ± 0.1 | 1.1 ± 0.1 | 0.0002 |
| Color (SalmoFan) | 27.4 ± 0.1 | 27.3 ± 0.1 | 0.5556 |
| Pigment mg/kg) | 7.8 ± 0.2 | 7.7 ± 0.1 | 0.5875 |
| Fat (%) | 18.9 ± 0.2 | 19.1 ± 0.2 | 0.5320 |
| pH, back | 6.08 ± 0.01 | 6.04 ± 0.01 | 0.052 |
| pH, NQC | 6.08 ± 0.01 | 6.05 ± 0.01 | 0.0316 |

The average strength (tensile strength) needed to break through the surface of the fillet for both diets was about 11 Newton, which is high. The firmness of the flesh as a whole was significantly higher for krill Group. Texture is a characteristic that shows considerable natural variation. For this fish material, parts of the fillets had soft muscle (≤6 Newton)

in the rear part of the fillet (NQC), and the percentage was higher for the control group (15%) than for Krill group (6%).

TABLE 4

| Attribute | Control group | Krill group | P value |
|---|---|---|---|
| Breaking strength surface (N) | | | |
| Back | 10.7 ± 0.3 | 11.1 ± 0.3 | 0.3729 |
| NQC | 7.8 ± 0.2 | 8.1 ± 0.2 | 0.2116 |
| Strength (N * s) | | | |
| Back | 238.3 ± 7.6 | 257.9 ± 6.9 | 0.0583 |
| NQC | 224.9 ± 6.7 | 247.4 ± 6.1 | 0.0148 |
| Fillet Thickness (mm) | | | |
| Back | 34.9 ± 0.5 | 36.3 ± 0.4 | 0.0339 |
| NQC | 25.7 ± 0.3 | 26.9 ± 0.3 | 0.0129 |

Andersen, U. B., Strømsnes, A. N., Steinsholt, K., Thomassen, M. S., 1994. Fillet gaping in farmed Atlantic salmon (Salmo salar). Norwegian Journal of Agricultural Sciences 8, 165-479.

Folkestad, A., Wold, J. P., Rørvik, K. A., Tschudi, J., Haugholt, K. H., Kolstad, K., Morkore, T., 2008. Rapid and non-invasive measurements of fat and pigment concentrations in live and slaughtered Atlantic salmon (Salmo salar L.). Aquaculture 280, 129-135.

Midtlyng, P. J., Reitan, Speilberg, L. J, 1996. Experimental studies on the efficacy and side-effects of intraperitoneal vaccination of Atlantic salmon (Salmo salar L.) against furunculosis. Fish & Shellfish Immunology 6, 335-350.

Mørkøre, T., Einen, O., 2003. Relating sensory and instrumental texture analyses of Atlantic salmon. Journal of Food Science 68, 14924497.

All publications and patents mentioned in the above specification are herein incorporated by reference. Various modifications and variations of the described compounds, compositions, methods and uses of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the biological and fishery sciences are intended to be within the scope of the following claims.

What is claimed is:

1. A method of decreasing fillet gaping in fillets obtained from Salmo salar comprising: feeding a population of Salmo salar from about 14 months of age to harvest at a mean weight of about 4 to 5 kilograms an effective amount of dietary ration comprising *Euphausia superba* krill meal; wherein the krill meal is provided in an amount of from 4% to 15% of the ration, said ration further comprising from 5% to 50% w/w fish meal, 5% to 30% w/w vegetable oil, and 5% to 15% w/w fish oil, so that the ration has a crude protein content of from about 32% to 46%, a crude lipid content of from about 26% to 42%, a carbohydrate (NFE) content of from about 11% to 18%, a fiber content of from about 1% to 5%, an ash content of from about 4% to 7%, a total phosphorus content (P) of from about 0.5% to 1.1%, a gross energy content of from about 20 to 30 MJ/kg, and a digestible energy content of from about 20 to 24 MJ/kg, and harvesting fillets from said population of Salmo salar, wherein fewer than 10% of fillets from fish from said population have gaping score of greater than 2.0 points (visible cleavage).

2. The method of claim 1, wherein said ration is a pelleted ration.

3. The method of claim 1, wherein said krill meal comprises an antioxidant.

4. The method of claim 3, wherein said antioxidant is a synthetic antioxidant.

5. The method of claim 4, wherein said synthetic antioxidant is ethoxyquin.

* * * * *